(12) United States Patent
Weinmann et al.

(10) Patent No.: US 11,865,612 B2
(45) Date of Patent: Jan. 9, 2024

(54) METAL POWDER FOR 3D-PRINTING

(71) Applicant: TANIOBIS GMBH, Goslar (DE)

(72) Inventors: Markus Weinmann, Goslar (DE);
Holger Brumm, Goslar (DE);
Christoph Schnitter, Holle (DE);
Melanie Stenzel, Schleswig (DE)

(73) Assignee: TANIOBIS GMBH, Goslar (DE)

( * ) Notice: Subject to any disclaimer, the term of this patent is extended or adjusted under 35 U.S.C. 154(b) by 108 days.

(21) Appl. No.: 17/047,069

(22) PCT Filed: Apr. 9, 2019

(86) PCT No.: PCT/EP2019/058901
§ 371 (c)(1),
(2) Date: Oct. 13, 2020

(87) PCT Pub. No.: WO2019/197376
PCT Pub. Date: Oct. 17, 2019

(65) Prior Publication Data
US 2022/0023941 A1    Jan. 27, 2022

(30) Foreign Application Priority Data

Apr. 13, 2018  (EP) .................................... 18167328

(51) Int. Cl.
*B22F 1/052*     (2022.01)
*B33Y 70/00*     (2020.01)
(Continued)

(52) U.S. Cl.
CPC ............ *B22F 1/052* (2022.01); *A61L 27/047* (2013.01); *A61L 27/06* (2013.01); *B22F 1/065* (2022.01); *B22F 9/082* (2013.01); *B22F 10/25* (2021.01); *B22F 10/28* (2021.01); *B22F 10/34* (2021.01); *B33Y 70/00* (2014.12); *C22C 14/00* (2013.01);
(Continued)

(58) Field of Classification Search
CPC .......... B22F 1/052; B22F 1/065; C22C 14/00; C22C 27/02
See application file for complete search history.

(56) References Cited

U.S. PATENT DOCUMENTS 5,871,595 A    2/1999 Ahmed et al.
6,607,693 B1   8/2003 Saito et al.
(Continued)

FOREIGN PATENT DOCUMENTS

CA    2331707 C  *  5/2010  ............ B22F 1/0014
CN    1483207 A     3/2004
(Continued)

OTHER PUBLICATIONS

Yin, J. O., et al. "Microstructural characterization and properties of Ti-28Ta at.% powders produced by plasma rotating electrode process." journal of Alloys and Compounds 713 (2017): 222-228. (Year: 2017).*

(Continued)

*Primary Examiner* — Sally A Merkling
*Assistant Examiner* — Sean P. O'Keefe
(74) *Attorney, Agent, or Firm* — Norman B. Thot

(57) ABSTRACT

The present invention relates to metal powders which are suitable to be employed in 3D printing processes as well as a process for the production of said powders.

18 Claims, 8 Drawing Sheets

(51) Int. Cl.
  *B22F 1/065* (2022.01)
  *B22F 9/08* (2006.01)
  *C22C 14/00* (2006.01)
  *B22F 10/28* (2021.01)
  *A61L 27/04* (2006.01)
  *A61L 27/06* (2006.01)
  *B22F 10/25* (2021.01)
  *B22F 10/34* (2021.01)
  *B33Y 10/00* (2015.01)
  *B33Y 80/00* (2015.01)

(52) U.S. Cl.
  CPC ..... *B22F 2301/205* (2013.01); *B22F 2304/10* (2013.01); *B33Y 10/00* (2014.12); *B33Y 80/00* (2014.12)

(56) References Cited

U.S. PATENT DOCUMENTS

| | | |
|---|---|---|
| 2011/0307014 A1 | 12/2011 | Niinomi et al. |
| 2016/0074942 A1 | 3/2016 | Fang et al. |
| 2016/0332232 A1 | 11/2016 | Forbes Jones et al. |
| 2017/0113273 A1 | 4/2017 | Fang et al. |
| 2018/0258512 A1 | 9/2018 | Sing et al. |

FOREIGN PATENT DOCUMENTS

| | | |
|---|---|---|
| CN | 105451916 A | 3/2016 |
| CN | 107598166 A | 1/2018 |
| CN | 107635701 A | 1/2018 |
| EP | 1 114 876 A1 | 7/2001 |
| EP | 1 447 823 A1 | 8/2004 |
| JP | 2003-224010 A | 8/2003 |
| JP | 2004-156134 A | 6/2004 |
| JP | 2017-520678 A | 7/2017 |
| JP | 2018-502218 A | 1/2018 |
| WO | WO-2016182631 A1 * | 11/2016 ............ B22F 1/0011 |
| WO | WO 2017/048199 A1 | 3/2017 |

OTHER PUBLICATIONS

Weinmann, M., et al. "Development of bio-compatible refractory Ti/Nb (/Ta) alloys for application in patient-specific orthopaedic implants." International Journal of Refractory Metals and Hard Materials 75 (2018): 126-136 (Year: 2018).*

A. Strondl et al.: "Characterization and Control of Powder Properties for Additive Manufacturing", JOM, vol. 67, No. 3, pp. 549-554 (2015).

ASTM Designation: B 527-06: "Standard Test Method for Determination of Tap Density of Metallic Powders and Compounds", pp. 1-3 (2006).

ASTM Designation: B 213-11: "Standard Test Methods for Flow Rate of Metal Powders Using the Hall Flowmeter Funnel", pp. 1-4 (2011).

ASTM Designation B 822-97: "Standard Test Method for Particle Size Distribution of Metal Powders and Related Compounds by Light Scattering", pp. 1-3 (1997).

European Standard EN ISO 6892-1: "Metallic materials—Tensile testing—Part 1: Method of test at room temperature (ISO 6892-1:2009)", pp. 1-75 (2009).

* cited by examiner

METAL POWDER FOR 3D-PRINTING

CROSS REFERENCE TO PRIOR APPLICATIONS

This application is a U.S. National Phase application under 35 U.S.C. § 371 of International Application No. PCT/EP2019/058901, filed on Apr. 9, 2019 and which claims benefit to European Patent Application No. 18167328.6, filed on Apr. 13, 2018. The International Application was published in English on Oct. 17, 2019 as WO 2019/197376 A1 under PCT Article 21(2).

FIELD

The present invention relates to metal powders which are suitable to be employed in 3D printing processes as well as to a process for the production of the powders.

BACKGROUND 3D printing refers to processes in which material is joined or solidified under computer control to create a three-dimensional object, with material being added together (such as liquid molecules or powder grains being fused together). 3D printing is used in both rapid prototyping and additive manufacturing (AM). Objects can be of almost any shape or geometry and are typically produced using digital model data from a 3D model or another electronic data source such as an Additive Manufacturing File (AMF) file (usually in sequential layers). There are many different technologies, for example, stereolithography (STL) or fused deposit modeling (FDM). Unlike material removed from a stock in the conventional machining process, i.e., subtractive manufacturing, 3D printing or AM thus builds a three-dimensional object from computer-aided design (CAD) model or AMF file, usually by successively adding material layer by layer.

In the current scenario, 3D printing or AM has been used in manufacturing, medical, industry and sociocultural sectors which facilitate 3D printing or AM to become a successful commercial technology.

One application field for devices generated via 3D printing is the medical sector where not only the precise manufacturing of surgical instruments but also custom-made medical devices are of high demand. Virtual planning of surgery and guidance using 3D printed, personalized instruments have been applied to many areas of surgery including total joint replacement and craniomaxillofacial reconstruction with great success. One example of this is the bioresorbable trachial splint to treat newborns with tracheobronchomalacia developed at the University of Michigan. Hearing aids and dental industries are expected to be the biggest area of future development using the custom 3D printing technology.

Patient-matched implants were a natural extension of this work, leading to truly personalized implants that fit one unique individual. The use of additive manufacturing for serialized production of orthopedic implants (metals) is also increasing due to the ability to efficiently create porous surface structures that facilitate osseointegration.

However, in spite of the ongoing development in the field, issues remain that still need to be addressed, in particular concerning the production of patient-matched implants.

Orthopedic implant materials are exposed to high mechanical loadings. Although conventional materials based on stainless steel or cobalt-chromium alloys display adequate mechanical strength, their employment raises toxicological concerns due to the release of toxic or allergenic elements, resulting in inflammatory reactions in the adjacent tissue. Metals and metal alloys based on titanium, tantalum and niobium show a higher biocompatibility with appropriate mechanical properties for avoiding stress-shielding and consecutive implant loosing. However, most of the metal powders available suffer from the drawback that their employment as materials in 3D printing processes did not to date result in products with the expected quality.

US 2016/0074942 describes a method for producing substantially spherical metal powders. The method includes providing a particulate source metal including a primary particulate and having an average starting particle size; mixing the particulate source metal with a binder and an optional solvent to form a slurry; granulating the slurry to form substantially spherical granules, wherein each granule comprises an agglomeration of particulate source metal; debinding the granules at a debinding temperature to reduce the binder content of the granules forming the debinded granules; at least partially sintering the debinded granules at a sintering temperature so that particles within each granule fuse together to form partially or fully sintered granules; and recovering the sintered granules to form the substantially spherical metal powder.

WO 2017/048199 describes a titanium-tantalum alloy having a titanium content ranging from 10 wt.-% to 70 wt.-% and wherein the alloy has a body centered cubic structure. A method of forming a titanium-tantalum alloy is also described, the method comprising the steps of: (a) slicing a 3D CAD model of a part to be formed into a plurality of 2D image layers; (b) preparing a homogenous powder mixture of titanium powder and tantalum powder; (c) dispensing a layer of the powder mixture onto a processing bed; (d) performing a powder bed fusion of the layer of the powder mixture according to one of the 2D image layers in one of: a vacuum environment and an inert gas environment; and performing steps (c) and (d) for each of the plurality of 2D image layers in succession.

However, despite all efforts made, a need remains for metal powders which are suitable for 3D printing that address the following issues:

The employment of metal powders in 3D printing process requires the powders to have certain properties. For example, the powders must be flowable in order to generate homogenous and pore-free articles. A certain particle size distribution is also usually required which may change depending on the particular 3D process used. The particle size distribution required for powders being employed in selective laser melting processes may thus be different from those intended to be employed in electron beam melting processes. Low contents of oxygen, nitrogen and hydrogen in the powders are additionally favorable to improve the mechanical properties of the later article. Last but not least, the employed powder should possess sufficient adsorption for laser light of distinct wave lengths or electron beams to allow for a sufficient melting which is required for the production of mechanically stable and pore-free articles. There is accordingly still the need for powders which are especially designed for the employment in 3D printing processes as well as processes for producing the powders.

SUMMARY

An aspect of the present invention is to provide a metal powder which is suitable for use in 3D printing processes, wherein the particles of the metal powder has an average aspect ratio $\Psi_A$ from 0.7 to 1, for example, from 0.8 to 1, for example, from 0.9 to 1, for example, from 0.95 to 1, with $\Psi_A = x_{Feret,min}/x_{Feret,max}$.

In an embodiment, the present invention provides a metal powder which is suitable for use in a 3D printing process. The metal powder includes a metal selected from the group consisting of tantalum, titanium and niobium, and alloys of tantalum, titanium and niobium. Particles of the metal powder comprise an average aspect ratio $\Psi_A$ of from 0.7 to 1, wherein $\Psi_A = x_{Feret\ min}/x_{Feret\ max}$.

BRIEF DESCRIPTION OF THE DRAWINGS

The present invention is described in greater detail below on the basis of embodiments and of the drawings in which.

DETAILED DESCRIPTION

Figure 1:
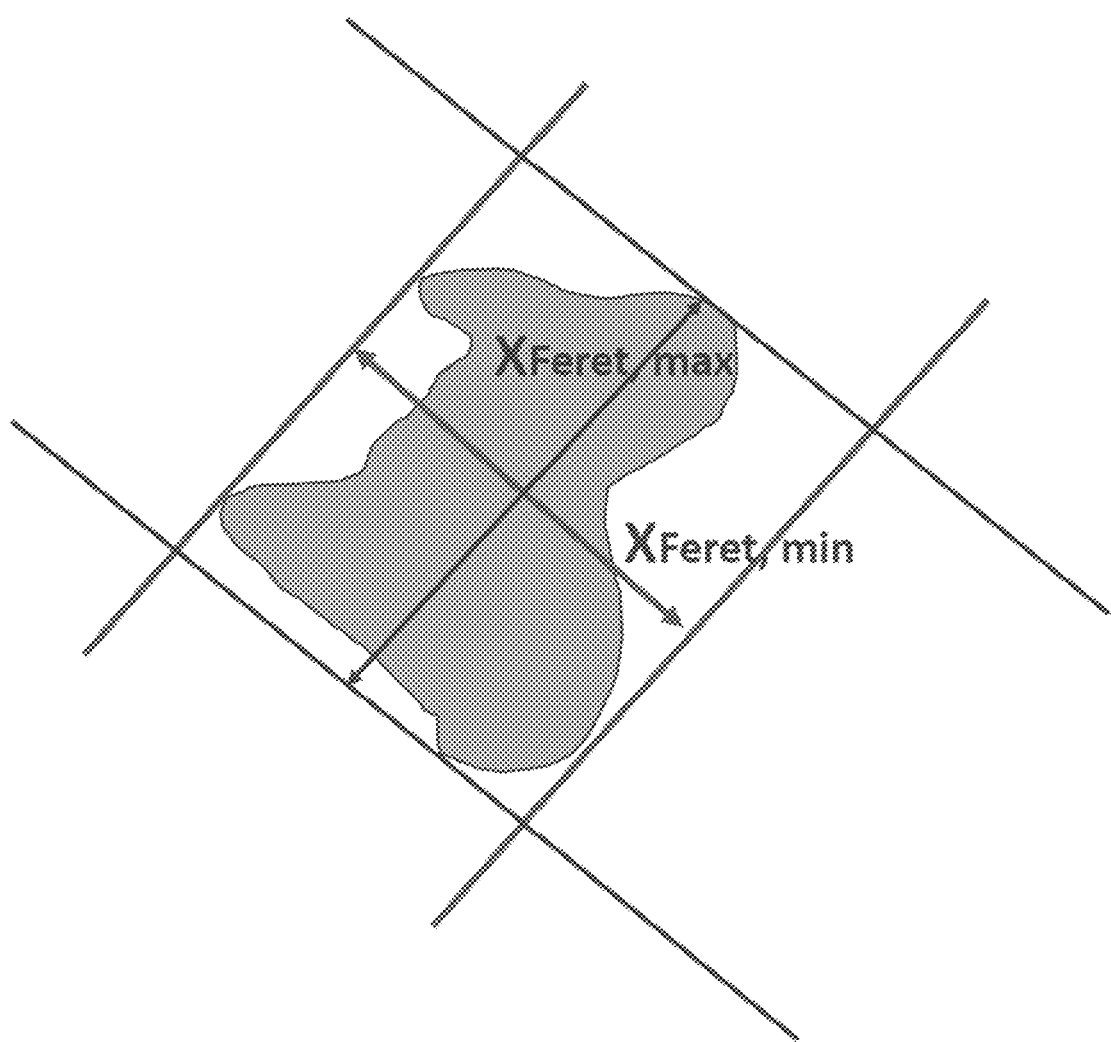
FIG. 1 shows a graphical representation of the definition of the Feret diameter as explained below.
Figure 2:
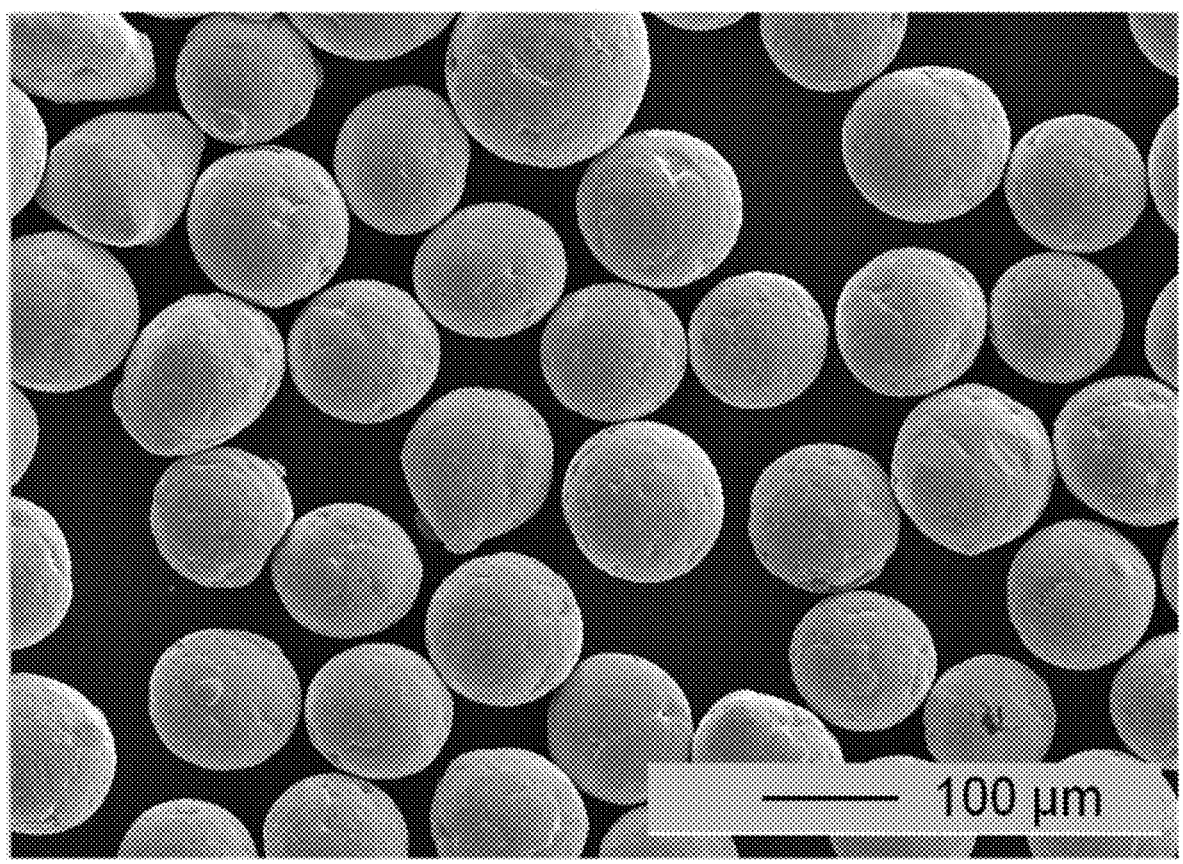
FIG. 2 shows a SEM image of the inventive powder according to Example 2. The particles possess a homogenous sphericity and particle size distribution.
Figure 3:
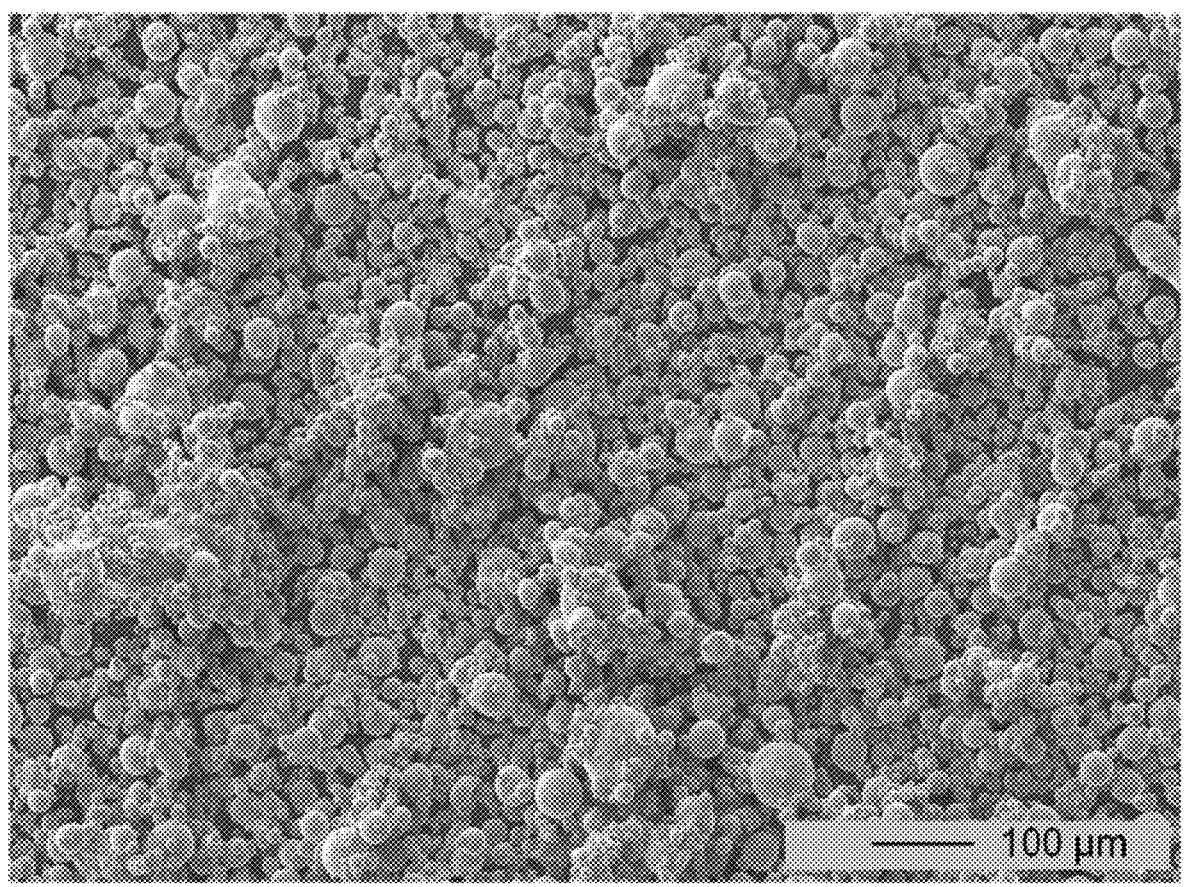
FIG. 3 shows a SEM image of the powder according to Comparative Example 4. In contrast to the inventive powder, the common powder shows a high degree of agglomeration, thus being unsuitable for use in 3D printing.
Figure 4:
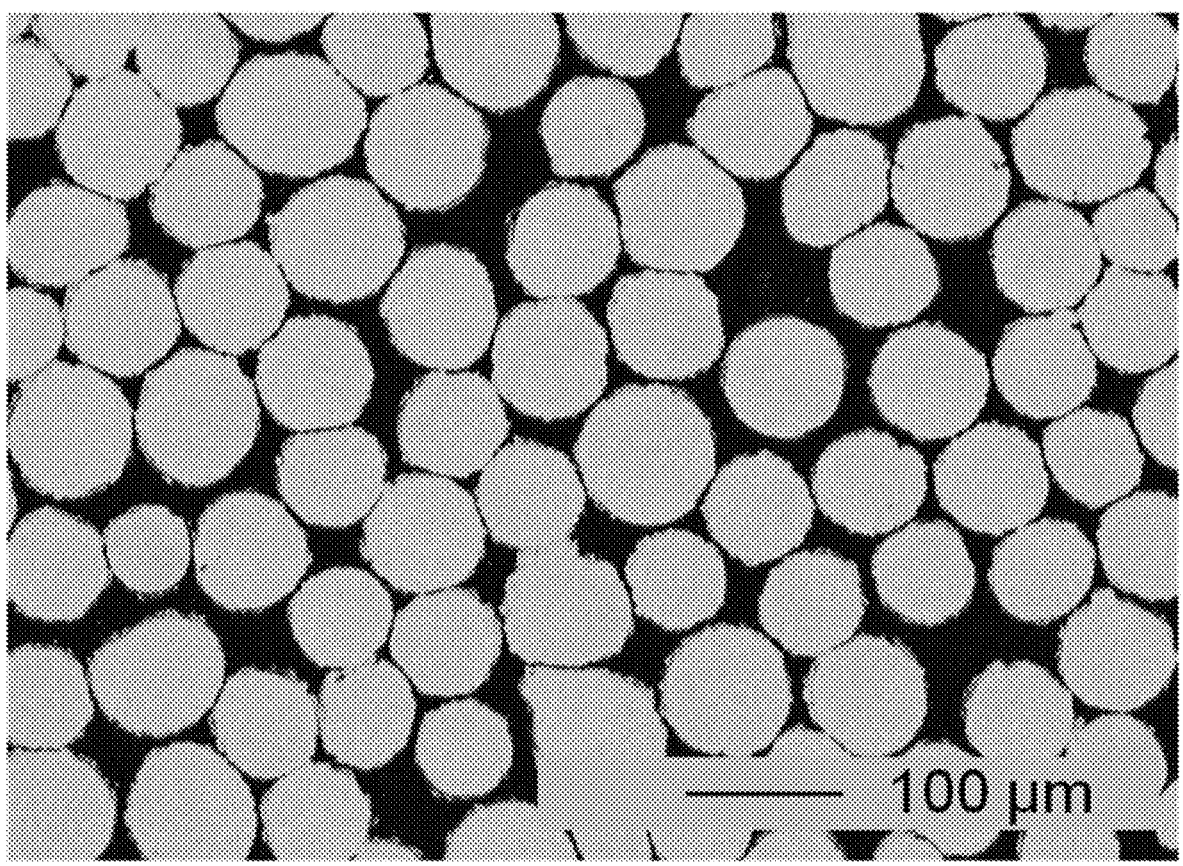
FIG. 4 shows a SEM (cross section) image of the inventive powder according to Example 11 which clearly shows the uniformity of the powder and the absence of any undesired particles with sizes that would render the powder unsuitable for 3D printing processes.
Figure 5:
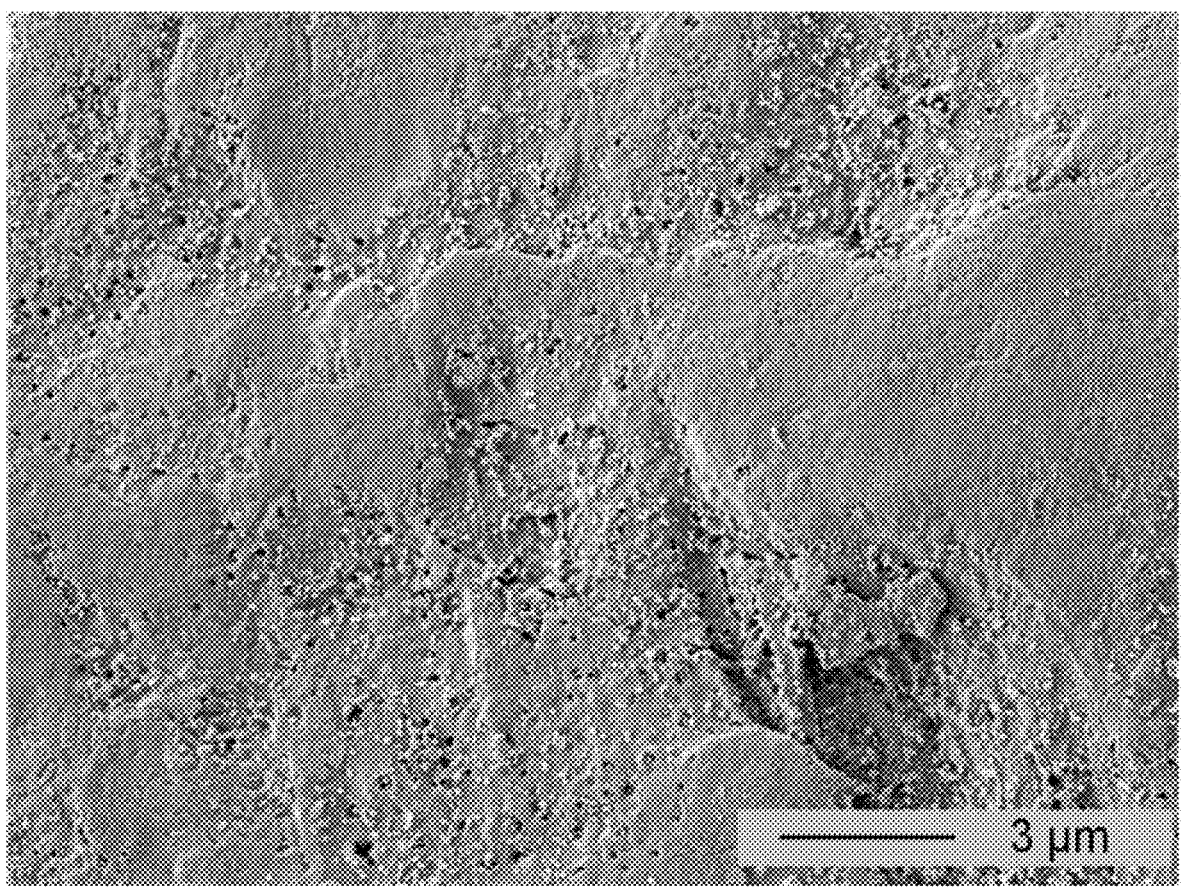
FIG. 5 shows an SEM image of the inventive powder according to Example 12 after treatment with HF which resulted in a roughening of the surface of the powder.
Figure 6:
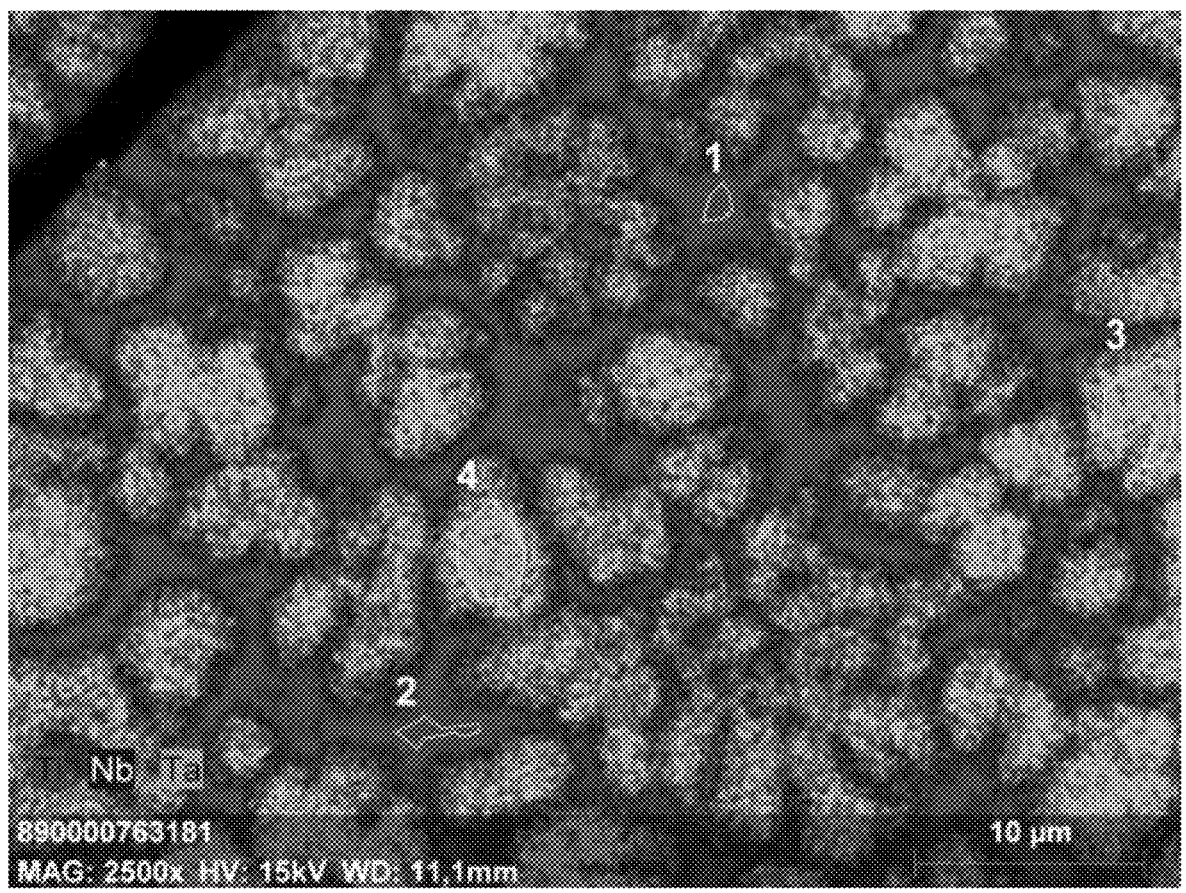
FIG. 6 shows an SEM image/EDX cross section of one powder particle of the inventive powder according to Example 11. The image clearly shows the dendritic character of the powder with:
1: Ti 70.8 wt %, Nb 26.3 wt %, Ta 2.9 wt %;
2: Ti 72.4 wt %, Nb 25.4 wt %, Ta 2.2 wt %;
3: Ti 54.0 wt %, Nb 38.2 wt %, Ta 7.8 wt %;
4: Ti 54.6 wt %, Nb 38.0 wt %, Ta 7.4 wt %.
Figure 7:
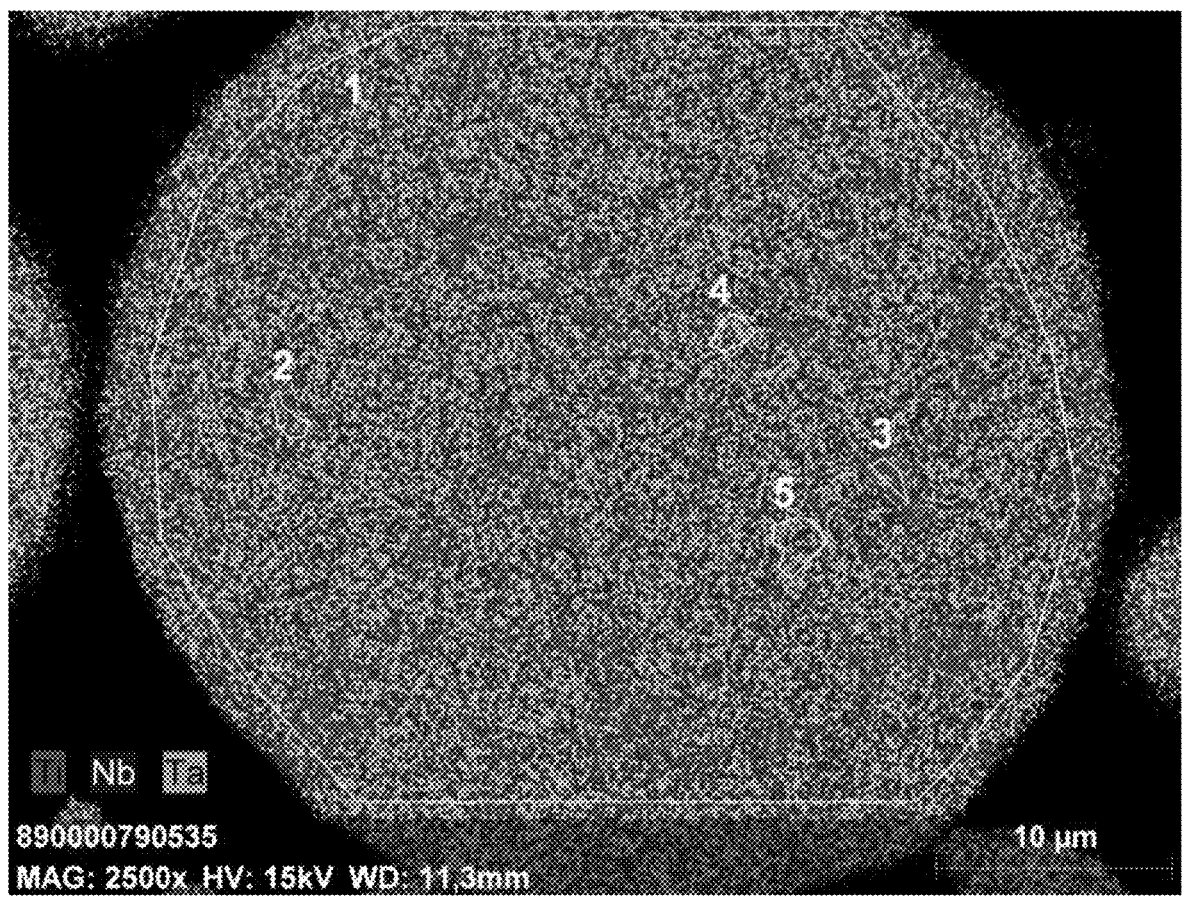
FIG. 7 shows an SEM image/EDX cross section of one powder particle of the inventive powder according to Example 13. The image clearly shows the dendritic character of the powder with:
1: Ti 56.4 wt %, Nb 40.0 wt %, Ta 3.6 wt %;
2: Ti 64.4 wt %, Nb 32.1 wt %, Ta 3.4 wt %;
3: Ti 67.4 wt %, Nb 31.4 wt %, Ta 1.2 wt %;
4: Ti 53.7 wt %, Nb 41.4 wt %, Ta 4.9 wt %;
5: Ti 53.5 wt %, Nb 42.0 wt %, Ta 4.5 wt %.

The Feret diameter is a measure of an object size along a specified direction. It can in general be defined as the distance between two parallel planes restricting the object perpendicular to that direction. This measure is used in the analysis of particle sizes, for example, in microscopy, where it is applied to projections of a three-dimensional (3D) object on a 2D plane. In such cases, the Feret diameter is defined as the distance between two parallel tangential lines rather than planes (see FIG. 1). With respect to the present invention, $\Psi_A$ is defined as the ratio of the minimal Feret diameter of a particle in μm and the maximum Feret diameter of the respective particle in μm. The average aspect ratio $\Psi_A$ within the meaning of the present invention refers to the distribution of aspect ratios of the particles of the powder, determined by statistical analysis of scanning electron microscopy (SEM).

It has surprisingly been found that particles with an average aspect ratio within the claimed range are especially suitable for employment in 3D printing process and possess a good flowability.

Metals such as tantalum (Ta), titanium (Ti) and niobium (Nb) are favorable materials for the production of orthopedic implants due to their low toxicity, high biocompatibility and high mechanical stability of the generated objects. In an embodiment of the present invention, the powder can, for example, comprise or consists of a metal that is selected from the group consisting of tantalum, titanium, niobium and alloys thereof. The powder according to the present invention can, for example, comprise an alloy of titanium and niobium. In an embodiment of the present invention, the alloy can, for example, further comprise tantalum. In an alternative embodiment, the powder can, for example, comprise an alloy of tantalum and niobium.

The composition of the powder may be adapted according to the requirements of the specific case. In an embodiment, the inventive metal powder can, for example, comprise an alloy powder which comprises Ti in an amount of 50 to 75 wt.-%, for example, 57 to 61 wt.-%, based on the total weight of the powder.

In an embodiment of the present invention, the inventive powder can, for example, comprise an alloy powder which comprises Nb in an amount of 25 to 50 wt.-%, for example, 39 to 43 wt.-%, based on the total weight of the powder.

In an embodiment of the present invention, the powder can, for example, comprise an alloy powder which comprises Ti in an amount of 50 to 75 wt.-%, for example, 57 to 61 wt.-% and Nb in an amount of 25 to 50 wt.-%, for example, 39 to 43 wt.-%, based on the total weight of the powder, respectively.

In an embodiment, the powder of the present invention can, for example, comprise an alloy of Ti, Nb and Ta. In such a case, the amount of Ta can, for example, be 2 to 20 wt.-%, for example, 2 to 15 wt.-%, for example, 2 to 6 wt.-%, based on the total weight of the powder. The alloy can, for example, comprise Ti in an amount of 50 to 75 wt.-%, for example, 55 to 70 wt %, for example, 55 to 61 wt.-%, Nb in an amount of 25 to 50 wt.-%, for example, 27 to 43 wt.-%, adding up to 100 wt.-% based on the total weight of the powder, respectively.

It has been found that the mechanical properties, such as the elasticity of objects, in particular orthopedic implants, can be much improved if the content of certain impurities is kept as low as possible. In an embodiment, the level of oxygen in the inventive powder can, for example, be less than 3000 ppm, for example, less than 1500 ppm and in particular less than 1000 ppm, for example, less than 500 ppm, for example, less than 300 ppm, ppm referring to the mass of the powder. The level of nitrogen in the inventive powder can, for example, be less than 200 ppm, for example, less than 100 ppm, for example, less than 50 ppm, for example, less than 30 ppm.

The content of lithium (Li), sodium (Na), potassium (K) in the inventive powder can, for example, be less than 80 ppm. It was surprisingly found that the quality of the generated products could be much improved if the content of these elements was kept below this level. In an embodiment, the content of Li in the inventive powder can, for example, be less than 80 ppm, for example, less than 50 ppm and in particular less than 30 ppm. In an embodiment, the content of Na in the inventive powder can, for example, be less than 80 ppm, for example, less than 50 ppm and in particular less than 30 ppm. In an embodiment of the present invention, the content of K can, for example, be less than 80 ppm, for example, 50 ppm and in particular less than 30 ppm. In an embodiment, the sum of the content of Li, Na and K in the inventive powder is less than 100 ppm, for example, less than 50 ppm.

In order for metal powders to be suitable for employment in 3D printing processes, the powders must possess a certain flowability as well as a certain tap density. In an embodiment, the inventive powder can, for example, have a tap density, determined according to ASTM B527, of 40-80% of its theoretical density, for example, 60-80%.

In case the inventive powder is a Ta, Nb or Ti metal powder or an alloy powder thereof, the powder can, for example, have a tap density of 1.8 to 13.3 g/cm$^3$, for example, 2.7 to 13.3 g/cm$^3$. For example, fully dense Tantalum has a density of 16.65 g/cm$^3$. The inventive Ta powder can, for example, accordingly have a tap density of 6.6 to 13.3 g/cm$^3$, for example, 10.0 to 13.3 g/cm$^3$. Fully dense niobium additionally has a density of 8.58 g/cm$^3$. In an embodiment, the inventive Nb powder can, for example, accordingly have a tap density of 3.4 to 6.9 g/cm$^3$, for example, 5.1 to 6.9 g/cm$^3$. In case the inventive powder comprises a binary alloy, particularly a Ti/Nb-alloy, the tap density can, for example, be from 2.2 to 5.2 g/cm$^3$, for example, 3.3 to 5.2 g/cm$^3$. In case the powder comprises a ternary alloy, in particular a Ti/Nb/Ta alloy, the powder can, for example, have a tap density of 2.3 to 6.5 g/cm$^3$, for example, 3.5 to 6.5 g/cm$^3$.

In an embodiment, the inventive powder can, for example, have a flowability of less than 25 s/50 g, especially less than 20 s/50 g, for example, less than 15 s/50 g, determined according to ASTM B213. It was surprisingly found that the inventive powders could be easily applied but still showed an appropriate steadfastness to allow the production of precise and clear edged articles.

As mentioned above, the particle size distribution of the inventive powder may be adapted according to need, in particular in accordance with the specific printing process used. Due to the different processing and requirements on the printed article, the demands with respect to the properties of the powder may differ according to the method used. For example, selective laser melting (SLM) uses fine powders to obtain accurately shaped articles with sufficiently resolved structural features. Electron beam melting (EBM) requires coarser particles, which is mainly a consequence of a repulsion of electrostatically charged particles as a consequence of their interaction with the electron beam. Such repulsion is explicitly pronounced for very fine powders. Laser cladding (LC) requires even coarser powders to avoid overspray and associated substantial powder loss.

In an embodiment, the inventive powder can, for example, have a particle size distribution of a D10 greater than 2 μm, for example, greater than 5 μm, and a D90 of less than 80 μm, for example, less than 70 μm, for example, less than 62 μm with a D50 of 20 to 50 μm, for example, 25 to 50 μm, determined according to ASTM B822. In an embodiment, the powder fraction obtained by classification by sieving is, for example, <63 μm. Such a powder is especially suitable for application in selective laser melting processes (SLM).

In an embodiment, the inventive powder can, for example, have a particle size distribution of a D10 greater than 20 μm, for example, greater than 50 μm, for example, greater than 65 μm and a D90 of less than 150 μm, for example, less than 120 μm, for example, less than 100 μm with a D50 of 40 to 90 μm, for example, 60 to 85 μm, determined according to ASTM B822. In an embodiment, the powder fraction obtained by classification by sieving can, for example, be 63 to 100 μm. Such a powder is especially suitable for application in electron beam melting processes (EBM).

In an embodiment, the inventive powder can, for example, have a particle size distribution of a D10 greater than 50 μm, for example, greater than 80 μm, for example, greater than 100 μm and a D90 of less than 240 μm, for example, less than 210 μm, with a D50 of 60 to 150 μm, for example, 100 to 150 μm, determined according to ASTM B822. In an embodiment, the powder fraction obtained by classification by sieving can, for example, be 100 to 300 μm. Such a powder is especially suitable for application in laser cladding processes (LC).

Figure 8:
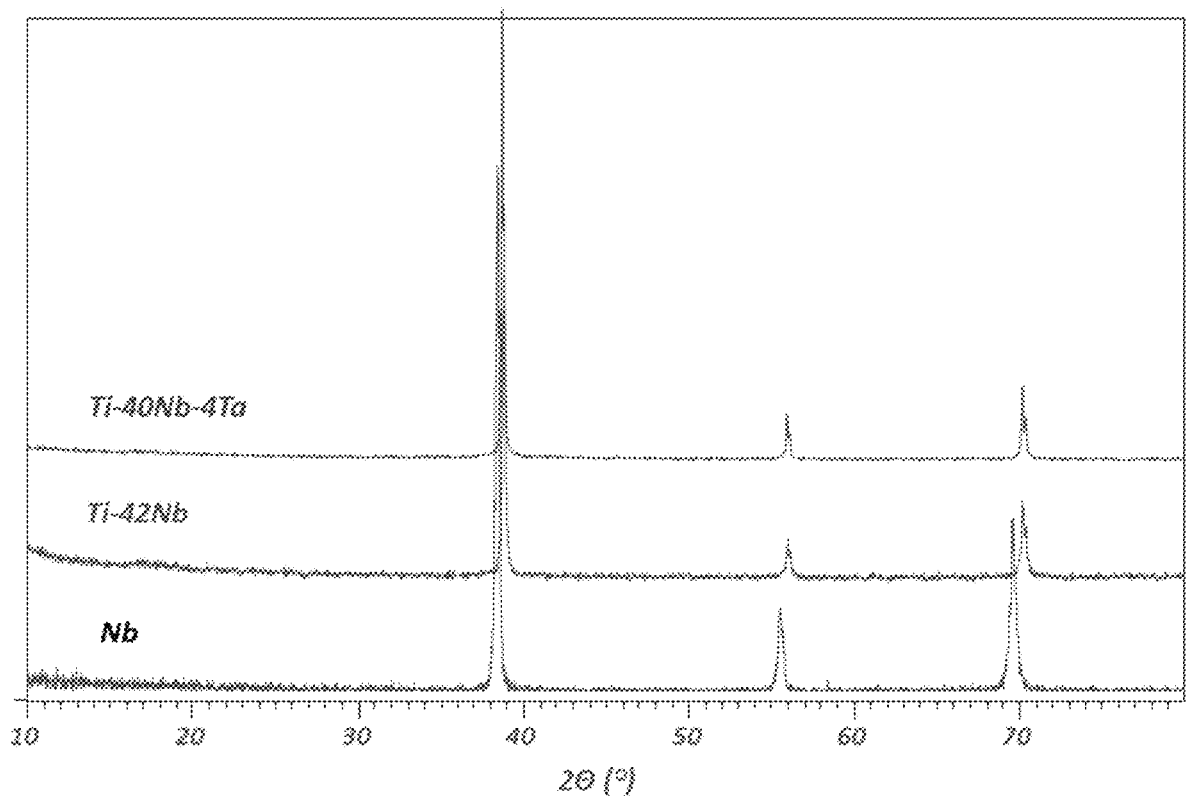
FIG. 8 shows X-ray diffraction diagrams of the inventive powders according to Examples 1 (Nb), 7 (Ti42Nb) and 13 (Ti40Nb4Ta). As can be clearly seen, only one crystallographic phase was identified in each diagram, even for the binary and ternary system.

It was surprisingly found that the mechanical stability as well as the homogeneity of elements distribution of an article generated by 3D printing processes can be greatly improved if the particles of the metal powder employed possess a dendritic microstructure. In an embodiment, the inventive powder can, for example, have a dendritic microstructure with local deviation in the chemical composition. Analysis of the inventive powder by X-ray diffraction surprisingly showed that the dendritic microstructure in the powder, although differing in composition, all had same crystalline structure in contrast to common powders where the local deviation of the composition is usually associated with different crystal structures resulting in more than one phase in the X-ray diffraction, whereas only one phase was detected in the case of the inventive powder. This is confirmed by FIG. 8 which shows a powder X-ray diffraction diagram of exemplary inventive powders.

The present invention also provides a process for the production of the inventive powder. The inventive process comprises the steps of:
  a) pressing or pressing and sintering the powdery components of the powder to obtain a metal body;
  b) atomizing the metal body to obtain a metal powder;
  c) separating of particles having a particle size of less than 2 μm, for example, less than 5 μm, for example, less than 10 μm, determined according to ASTM B822 to obtain the inventive metal powder; and
  d) classification of the particle sizes of the inventive metal powder via screening to obtain the desired particle size distribution.

It was surprisingly found that the process according to the present invention allows the production of metal powders which are especially suitable for 3D printing processes.

In an embodiment, the separating in step c) of the inventive process is provided by sifting, in particular via air classification of the powder.

In an embodiment, the separating in step c) of the inventive process can, for example, be provided by de-agglomeration in a water bath using ultra sound and subsequent decantation. In an embodiment, the de-agglomeration is provided by stirring in a water bath and subsequent decantation. In an embodiment, de-agglomeration is provided via high power dispersion in a water bath and subsequent decantation. High power dispersion may, for example, be carried out using an Ultra-Turrax®, available from IKA®-Werke GmbH & Co. KG, Germany.

In an embodiment, the degree of decantation of the fine particles can, for example, be adjusted by manipulation of the zeta-potential of the dispersion. This may, for example be achieved by adjustment of the pH-value. An embodiment of the inventive process therefore provides that the degree of decantation of the particles can, for example, be adjusted by adjusting the pH of the water bath used in deagglomeration.

It is desirable to obtain a metal powder with a low oxygen content. In an embodiment, the inventive process can, for example, therefore further comprise a step of deoxidation. The deoxidation of the inventive powder can, for example, be carried out subsequent to step c) of the inventive powder. Deoxidation can, for example, be carried out in the presence of a reducing agent, for example, a reducing agent selected from the group consisting of Li, Na, K, Mg and Ca as well as mixtures thereof. In an embodiment, the inventive powder can, for example, be subjected to a leaching step after deoxidation to remove any undesired impurities generated during deoxidation. Leaching can, for example, be conducted using an inorganic acid. In order to adjust the properties of the powder to match the requirements of the specific application, the surface of the powder can be doped. In an embodiment, the surface of the powder can therefore, for example, be doped, for example, with a doping agent selected from the group consisting of phosphorous, boron, silicon, yttrium, calcium, magnesium and mixtures thereof. The process of doping is well known to the person skilled in the art. The person skilled in the art is therefore well aware how the doping agent is to be introduced.

The inventive powder may further be manipulated in order to improve the performance in 3D printing processes. In an embodiment, the inventive powder can therefore, for example, be further subjected to an acid treatment, the acid can, for example, be hydrogen fluoride or complex-forming carboxylic acids. It was surprisingly found that the absorption of the laser radiation during the printing process can be improved if the powder is subjected to such an acid treatment. Without being bound by theory, it is believed that the treatment may lead to a roughening of the powder surface, thus increasing the surface absorption of radiation.

In an embodiment, the complex-forming carboxylic acid can, for example, be selected from the group consisting of carboxylic acid, dicarboxylic acid and alpha hydroxy acid as well as mixtures thereof.

The inventive powder is especially suitable for the application in 3D printing processes. The present invention therefore provides the use of the inventive powders in additive manufacturing processes. The process can, for example, be selected from the group consisting of selective laser melting (SLM or LBM), electron beam melting (EBM) and laser cladding (LC).

The present invention also provides a process for producing a three-dimensional article using the inventive powder, wherein the three-dimensional article is build-up layer by layer.

The present invention also provides a three-dimensional article obtained by the inventive process and/or comprising the inventive powder. The three-dimensional article is characterized by its favorable properties which make the three-dimensional article especially suitable for medicinal applications. The requirements for articles used for medicinal purposes are widely diversified, ranging from biocompatibility to mechanical strength. It was surprisingly found that three-dimensional articles produced from the powder according to the present invention, in particular using 3D printing processes, showed especially advantageous properties. The elastic modulus (Young's modulus, $m_E$) was found to be close to the one of natural bones which have an elastic modulus of around 40 GPa. Common materials presently used show a much higher elastic modulus of more than 100 GPa, leading to an inferior compatibility of the implant. It is therefore desirable, to obtain implants with properties much closer to those of the natural bone, an object achieved in the course of the present invention. In an embodiment, the three-dimensional article according to the present invention can therefore, for example, have an elastic modulus $m_E$ of 20 to 100 GPa, for example, 40 to 90 GPa, for example, 40 to 80 GPa, determined according to DIN EN ISO 6892-1.

In an embodiment, three-dimensional article according to the present invention can, for example, have an ultimate strength ($R_m$) of 600 to 1400 MPa, for example, 600 to 1200 MPa, in particular 600 to 699 MPa, determined according to DIN EN ISO 6892-1.

In an embodiment, the three-dimensional article according to the present invention can, for example, have a yield strength $R_{p0.2}$ of 500 to 1200 MPa, for example, 500 to 1000 MPa, in particular 500 to 699 MPa, determined according to DIN EN ISO 6892-1.

In an embodiment, the inventive three-dimensional article can, for example, have:
- an elastic modulus $m_E$ of 20 to 100 GPa, for example, 40 to 90 GPa, in particular 40 to 80 GPa, determined according to DIN EN ISO 6892-1;
- an ultimate strength $R_m$ of 600 to 1400 MPa, for example, 600 to 1200 MPa, in particular 600 to 699 MPa, determined according to DIN EN ISO 6892-1; and
- a yield strength $R_{p0.2}$ of 500 to 1200 MPa, for example, 500 to 1000 MPa, in particular 500 to 699 MPa, determined according to DIN EN ISO 6892-1.

In an embodiment, the inventive three-dimensional article can, for example, be characterized by a strain value $A_g$ at ultimate strength $R_m$ of more than 0.5%, for example, more than 1%, in particular more than 4%, determined according to DIN EN ISO 6892-1, respectively.

In an embodiment, the inventive three-dimensional article can, for example, have a value $A_{30}$ of strain at fracture of more than 2%, for example, more than 4%, in particular more than 10%, determined according to DIN EN ISO 6892-1, respectively.

The article can, for example, be an implant, in particular a medicinal implant, such as a dental implant, a hip implant, a knee implant, a shoulder implant, a craniofacial implant or a spine implant. In an embodiment, the article can, for example, be for high temperature applications, such as ovens and reactors.

The present invention will be explained in more detail with the help of the following examples which are not to be understood as limiting the present invention.

Examples

Several powders were prepared according to steps a) and b) of the described process. The results are summarized in Table 1:

TABLE 1

| | Material Class | Particle Size Distribution (PSD) by Laser Diffraction | | | Tap Density g/cc | Flow s/50 g | Chemical Analysis | | | $\Psi_A$ average aspect ratio |
|---|---|---|---|---|---|---|---|---|---|---|
| | | D10 μm | D50 μm | D90 μm | | | O ppm | N ppm | Mg ppm | |
| Com. 1 | Nb | 9 | 95 | 231 | 5.4 | 26 | 1618 | 79 | <10 | 0.69 |
| Com. 2 | Ta | 4 | 30 | 61 | 9.9 | 12 | 680 | 10 | <10 | 0.68 |
| Com. 3 | Ti42Nb | 8 | 64 | 131 | 3.2 | no flow | 2466 | 65 | <10 | 0.58 |
| Com. 4 | Ti27Nb6Ta | 9 | 63 | 148 | 2.2 | no flow | 3705 | 98 | <10 | 0.64 |
| Com. 5 | Ti40Nb4Ta | 7 | 37 | 80 | 2.7 | no flow | 2473 | 166 | <10 | 0.67 |

The obtained powders where subjected to a partition step as described in step c) of the inventive process, whereby:
1) sifting/air classification
2) ultrasonic treatment
3) water decantation (at pH 5 to 8)

The powders were subsequently de-oxidized and classified by sieving according the fractions given in Table 2. The results are summarized in Table 2:

$m_E$: elastic module, determined according to DIN EN ISO 6892-1:2016

$R_{p0.2}$: yield strength, determined according to DIN EN ISO 6892-1:2016

$R_m$: ultimate strength, determined according to DIN EN ISO 6892-1:2016

$F_m$: maximum force, determined according to DIN EN ISO 6892-1:2016

| Ex. | Composition | Deagglomeration Step c) | Deoxidation | Classification by sieving Step d) | Particle Size Distribution (PSD) by Laser Diffraction | | |
|---|---|---|---|---|---|---|---|
| | | | | | D10 [μm] | D50 [μm] | D90 [μm] |
| 1 | Nb | 1 | yes | <63 μm | 24 | 41 | 58 |
| 2 | Nb | 1 | yes | 63-100 μm | 69 | 83 | 95 |
| 3 | Nb | 1 | yes | 100-300 μm | 106 | 146 | 199 |
| 4 | Ta | 3 | yes | <63 μm | 15 | 30 | 55 |
| 5 | Ti42Nb | 3 | no | 100-300 μm | 110 | 130 | 174 |
| 6 | Ti42Nb | 3 | no | 63-100 μm | 63 | 77 | 98 |
| 7 | Ti42Nb | 3 | no | <63 μm | 18 | 39 | 61 |
| 8 | Ti42Nb | 3 | yes | 63-100 μm | 68 | 80 | 96 |
| 9 | Ti42Nb | 3 | yes | <63 μm | 23 | 42 | 60 |
| 10 | Ti27Nb6Ta | 3 | no | 100-300 μm | 103 | 137 | 187 |
| 11 | Ti27Nb6Ta | 3 | yes | 63-100 μm | 70 | 83 | 93 |
| 12 | Ti27Nb6Ta | 3 | yes | <63 μm | 25 | 49 | 60 |
| 13 | Ti40Nb4Ta | 3 | yes | <63 μm | 22 | 45 | 57 |
| 14 | Ti20Nb6Ta | 3 | yes | <63 μm | 24 | 45 | 62 |

| Ex. | Flow s/50 g | Tap Density g/cc | Chemical Analysis | | | | | $\Psi_A$ Average Aspect Ratio |
|---|---|---|---|---|---|---|---|---|
| | | | O ppm | H ppm | N ppm | Sum Li, Na, K ppm | Mg ppm | |
| 1 | 18 | 5.5 | 556 | 37 | 111 | <15 | 33 | 0.95 |
| 2 | 15 | 5.3 | 373 | 30 | 89 | <15 | 20 | 0.95 |
| 3 | 14 | 5.3 | 269 | 34 | 85 | <15 | 14 | 0.96 |
| 4 | 7 | 10 | 150 | 14 | 12 | <15 | 15 | 0.95 |
| 5 | 21 | 3.1 | 2574 | <10 | 103 | <15 | <10 | 0.92 |
| 6 | 23 | 3.5 | 2527 | <10 | 88 | <15 | <10 | 0.89 |
| 7 | 23 | 3.8 | 2584 | <10 | 49 | <15 | <10 | 0.88 |
| 8 | 13 | 3.4 | 837 | 245 | 167 | <15 | 141 | 0.95 |
| 9 | 15 | 3.6 | 960 | 258 | 165 | <15 | 30 | 0.95 |
| 10 | 22 | 3.6 | 2964 | 22 | 97 | <15 | <10 | 0.93 |
| 11 | 16 | 3.4 | 1398 | 17 | 91 | <15 | <10 | 0.96 |
| 12 | 19 | 3.9 | 1484 | 24 | 101 | <15 | 105 | 0.95 |
| 13 | 18 | 3.7 | 1470 | 35 | 140 | <15 | 140 | 0.95 |
| 14 | 20 | 3.8 | 1519 | 41 | 99 | <15 | 95 | 0.97 |

The inventive powders of Examples 9, 12, 13 and 14 were employed in a selective laser melting process to produce three-dimensional test articles 1, 2, 3 and 4, respectively, the properties of which were tested according to DIN EN ISO 6892-1:2016. The respective results are summarized in Table 3, the given values being the average results obtained over a series of tests.

$A_g$: strain at $R_m$, determined according to DIN EN ISO 6892-1:2016

$A_{30}$: strain at fracture, determined according to DIN EN ISO 6892-1:2016

$S_0$: area of cross section, determined according to DIN EN ISO 6892-1:2016

TABLE 3

| Article | Composition | No. of Tests | $m_E$ [GPa] | $R_{p0.2}$ [MPa] | $R_m$ [MPa] | $F_m$ [kN] | $A_g$ [%] | $A_{30}$ [%] | $S_0$ [mm$^2$] |
|---|---|---|---|---|---|---|---|---|---|
| 1 | Ti42Nb | 8 | 61 | 674 | 688 | 19.4 | 0.5 | 12.3 | 28.2 |
| 2 | Ti20Nb6Ta | 18 | 80 | 671 | 1100 | 31.0 | 5.0 | 15 | 28.2 |
| 3 | Ti27Nb6Ta | 19 | 59 | 698 | 828 | 23.4 | 1.3 | 4.1 | 28.3 |
| 4 | Ti40Nb6Ta | 19 | 54 | 796 | 864 | 24.4 | 0.6 | 2.5 | 28.3 |

The present invention is not limited to embodiments described herein; reference should be had to the appended claims.

What is claimed is:

1. A metal powder suitable for use in a 3D printing process, the metal powder comprising:
   a metal selected from an alloy consisting of tantalum, niobium and impurities, an alloy consisting of titanium, niobium and impurities, and an alloy consisting of tantalum, titanium, niobium and impurities,
   wherein,
   particles of the metal powder have a dendritic microstructure, and
   particles of the metal powder comprise an average aspect ratio $\Psi_A$ of from 0.7 to 1, where $\Psi_A = x_{Feret\ min}/x_{Feret\ max}$.

2. A metal powder suitable for use in a 3D printing process, the metal powder consisting of:
   a metal selected from the group consisting of,
      tantalum and impurities,
      titanium and impurities,
      niobium and impurities,
      an alloy consisting of tantalum, niobium and impurities,
      an alloy consisting of titanium, niobium and impurities, and
      an alloy consisting of tantalum, titanium, niobium and impurities,
   wherein,
   particles of the metal powder have a dendritic microstructure, and
   particles of the metal powder comprise an average aspect ratio $\Psi_A$ of from 0.7 to 1, where, $\Psi_A = x_{Feret\ min}/x_{Feret\ max}$.

3. A metal powder suitable for use in a 3D printing process, the metal powder consisting of:
   a metal selected from the group consisting of,
      tantalum and impurities,
      titanium and impurities,
      niobium and impurities,
      an alloy consisting of tantalum, niobium and impurities,
      an alloy consisting of titanium, niobium and impurities, and
      an alloy consisting of tantalum, titanium, niobium and impurities,
   wherein,
   particles of the metal powder have a dendritic microstructure,
   particles of the metal powder comprise an average aspect ratio $\Psi_A$ of from 0.7 to 1, where $\Psi_A = x_{Feret\ min}/x_{Feret\ max}$, and
   the impurities are <3,440 ppm.

4. The metal powder as recited in claim 3, wherein the metal powder consists of the alloy consisting of titanium, niobium and impurities.

5. The metal powder as recited in claim 3, wherein the metal powder consists of the alloy consisting of tantalum, niobium ad impurities.

6. The metal powder as recited in claim 3, wherein the metal powder consists of the alloy consisting of titanium, niobium, tantalum and impurities.

7. The metal powder as recited in claim 3, wherein the metal powder has a tap density of 40 to 80% of a theoretical density of the metal powder, each determined according to ASTM B527.

8. The metal powder as recited in claim 3, wherein the metal powder has a flowability of less than 25 s/50 g, determined according to ASTM B213.

9. The metal powder as recited in claim 3, wherein the metal powder has,
   a particle size distribution D10>2 µm,
   a particle size distribution D90<80 µm, and
   a particle size distribution D50 of 20 to 50 µm,
   each determined according to ASTM B822.

10. The metal powder as recited in claim 3, wherein the metal powder has,
    a particle size distribution D10 of >20 µm,
    a particle size distribution D90 of <150 µm, and
    a particle size distribution D50 of 40 to 90 µm,
    each determined according to ASTM B822.

11. The metal powder as recited in claim 3, wherein the metal powder has,
    a powder distribution D10 of >50 µm,
    a powder distribution D90 of <240 µm, and
    a powder distribution D50 of 60 to 150 µm,
    each determined according to ASTM B822.

12. The metal powder as recited in claim 3, wherein the impurities consist of:
    oxygen being ≤3000 ppm,
    nitrogen being ≤200 ppm,
    lithium being ≤80 ppm
    sodium being ≤80 ppm, and
    potassium being ≤80 ppm.

13. A process for producing the metal powder as recited in claim 3, the process comprising:
    pressing or pressing and sintering powdery components of the metal powder to obtain a metal body;
    atomizing the metal body to obtain a metal powder;
    separating out particles of the metal powder having a particle size of <2 µm, determined according to ASTM B822; and
    screening so as to classify particle sizes of the metal powder.

14. The process as recited in claim 13, wherein the separating out of the particles of the metal powder having the particle size of <2 µm is performed by sifting the metal powder.

15. The process as recited in claim 13, wherein the separating out of the particles of the metal powder having the particle size of <2 µm is performed by de-agglomeration of the metal powder in a water bath using ultra sound and a subsequent decantation.

16. The process as recited in claim 13, wherein the separating out of the particles of the metal powder having the particle size of <2 µm is performed by stirring the metal powder in a water bath and a subsequent decantation.

17. The process as recited in claim 13, wherein the process further comprises:
 a deoxidation step.

18. The process as recited in claim 13, wherein the metal powder is further subjected to an acid treatment.

* * * * *